(12) United States Patent  (10) Patent No.: US 6,358,196 B1
Rayman  (45) Date of Patent: Mar. 19, 2002

(54) MAGNETIC RETRACTION SYSTEM FOR LAPAROSCOPIC SURGERY AND METHOD OF USE THEREOF

(76) Inventor: Reiza Rayman, 19 King Street, Suite 701, London, Ontario (CA), NBA 5N8

( * ) Notice: Subject to any disclaimer, the term of this patent is extended or adjusted under 35 U.S.C. 154(b) by 0 days.

(21) Appl. No.: 09/474,924

(22) Filed: Dec. 29, 1999

(51) Int. Cl.$^7$ .............................................. A61B 18/18
(52) U.S. Cl. ........................................... 600/12; 600/9
(58) Field of Search ............................. 600/12, 13, 15, 600/9, 14, 201

(56) References Cited

U.S. PATENT DOCUMENTS

| | | | |
|---|---|---|---|
| 2,103,440 A | * 12/1937 | Weissenberg | ................... 600/9 |
| 3,890,953 A | * 6/1975 | Kraus et al. | ................... 600/12 |
| 4,364,377 A | * 12/1982 | Smith | ........................... 600/12 |
| 4,682,600 A | * 7/1987 | Haas et al. | ..................... 600/9 |
| 5,529,568 A | * 6/1996 | Rayman | ......................... 600/9 |
| 5,555,897 A | * 9/1996 | Lathrop, Jr. et al. | ......... 600/201 |
| 5,593,379 A | * 1/1997 | Rayman | ......................... 600/9 |
| 5,667,469 A | * 9/1997 | Zhang et al. | ................... 600/9 |
| 5,788,624 A | * 8/1998 | Lu et al. | ......................... 600/9 |

* cited by examiner

*Primary Examiner*—Paul J. Hirsch
(74) *Attorney, Agent, or Firm*—R.W. Becker & Associates; R. W. Becker

(57) ABSTRACT

A novel magnetic retraction system is provided herein. The magnetic retraction system includes magnetic means for applying a magnetic field around a defined area of the magnetic retraction system. An articulatable support is provided for such magnetic means. The magnetic means includes an upper (North) magnetic pole. A lower (South) magnetic pole is induced in the intestine of a patient into which has been introduced a magnetic or magnetizable material. The induced lower pole is spaced a selectable spaced distance from the upper (North) magnetic pole. The upper pole may have its strength and/or the orientation of its magnetic field varied to adjust and/or to manipulate the intestine.

19 Claims, 4 Drawing Sheets

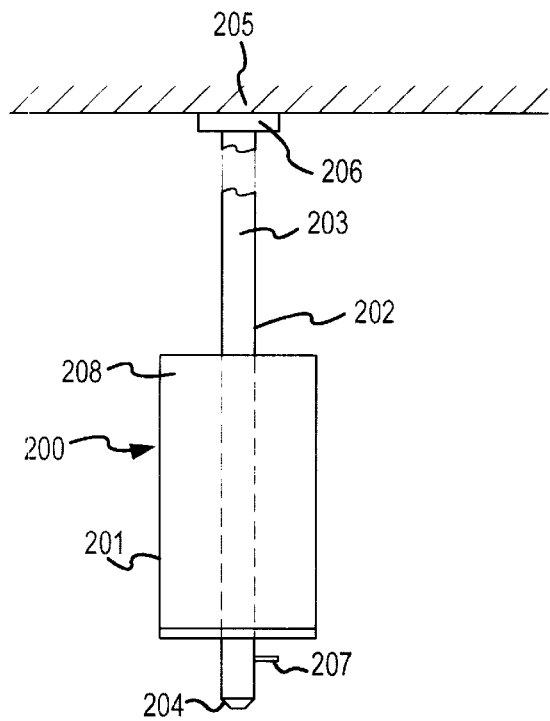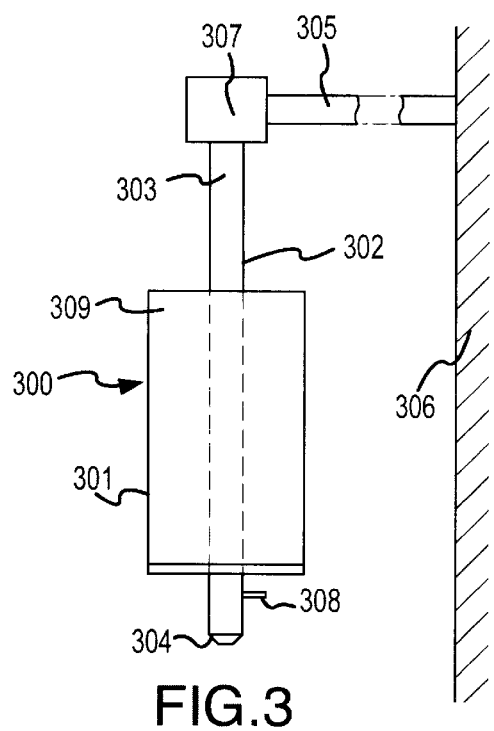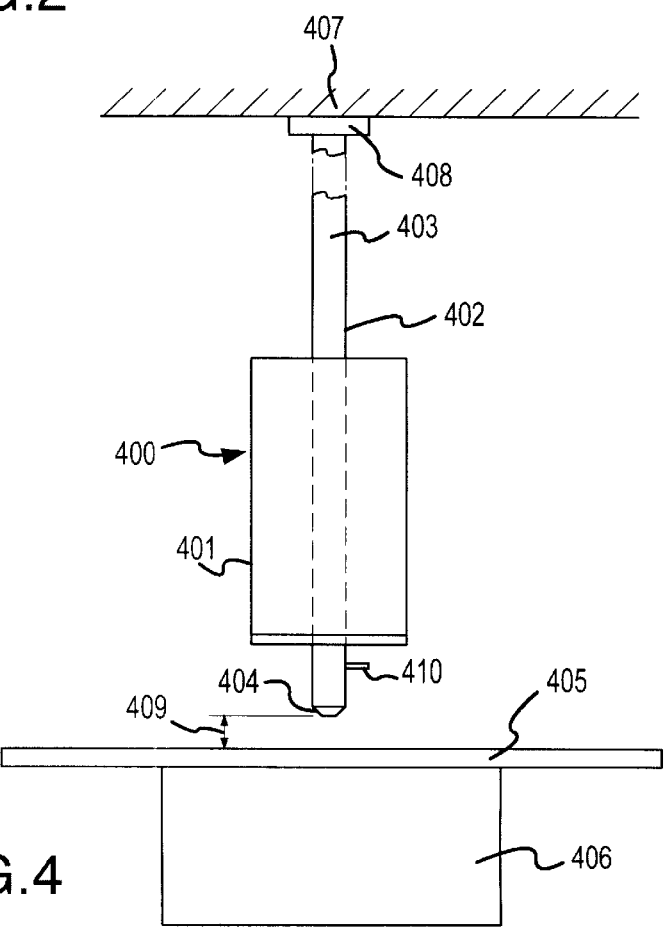

MAGNETIC RETRACTION SYSTEM FOR LAPAROSCOPIC SURGERY AND METHOD OF USE THEREOF

Related Invention

This application is related to Applicant's U.S. Pat. No. 5,529,568, patented Jun. 25, 1996 and U.S. Pat. No. 5,593,379, patented Jan. 14, 1997.

BACKGROUND OF THE INVENTION

1. Field of the Invention

This invention relates to a magnetic retraction system which is especially useful for laparoscopic surgery, and to a method of assisting in the performance of laparoscopic surgery using such magnetic retraction system.

2. Description of the Prior Art

Surgery continues to develop based partially on science, but is significantly anchored by tradition. Traditionally, surgery has been performed by the use of mechanical energy to manipulate tissue. Any clamping, grasping, cutting, or tying of tissues is effectively mechanical energy which is applied to that tissue. However, entire spectrums of energy remain unused and unexplored.

Energy spectrums available for consideration in surgery include tissue manipulation by the following means: mechanical (most widely used); electrical/heat (e.g., electrocautery); pressure (e.g., insufflation; suction); light (unused); radio (unused); magnetic/electromagnetic (unused); sound (unused); kinetic (unused); and chemical/molecular (unused).

Laparoscopic surgery is changing the way surgery in the abdomen is done. Instead of large incisions, multiple thin, long-handled instruments and one long camera scope are placed through very small (about 2 mm to about 3 mm) incisions. Surgery is done using the television view (which is provided by the camera scope) in conjunction with the long-handled instruments that extend from the surgical site, outside the body, and to the hands of the surgeon. Such mini-incisions greatly decrease surgical complications and post-surgical recovery periods. In this type of surgery, manipulation is performed by means of thin instruments extending from within the body to outside the body, thus eliminating the need for full abdominal incisions. A long camera scope is used to visualize surgical manipulations within the body.

Currently, the intestine is adjusted laparoscopically using long gripping instruments. This method is quite tedious and time consuming. It would therefore be an improvement if the intestine could be adjusted by the use of means other than mechanical gripping, e.g., by the use of magnetic means following the ingestion of magnetic or magnetizable materials.

The concept of the use, by ingestion or otherwise, of magnetic or magnetizable materials in conjunction with medical and/or surgical techniques is known. For example U.S. Pat. No. 2,671,451, patented Mar. 9, 1959, by S. J. Bolger, titled "Remedial Pill", provided a remedial pill comprising a remedial substance which was soluble in the human body and a magnetically-attractable metallic element associated with the substance. In use, a magnet was applied to the exterior of the body and the remedial pill was ingested. The pill travelled to the area of the magnet, where it was attracted and held. The remedial substances then dissolved. This patent was not concerned with adjusting or manipulating of the intestines, e.g., with retraction, suspension or longitudinal translation of intestine segments to assist in the performance of laparoscopic surgery. On the other hand, this patent was merely directed to the treatment of localized disorders of the alimentary canal, particularly ulcers, where it was very difficult to apply a remedy to the affected spot for the reason that there was a constant flow through the alimentary canal caused by the normal digestive processes.

U.S. Pat. No. 3,043,309, patented Jul. 10, 1962, by H. F. McCarthy, titled "Method of Performing Intestinal Intubation", provided a method and means for performing intestinal intubation. The method involved securing a magnetic member to the tip of an elongated, X-ray opaque, flexible tube. The tip and tube were then passed through the oesophagis to the stomach of a patient. The stomach region was then illuminated by means of X-rays, and the tube was observed on a fluoroscopic screen. A maneuverable magnetic field was then applied to the magnetic material to direct the tip, to which the magnetic material was secured, to the pylorus valve in the stomach. A highly flexible intubation tube was adapted to pass through the intestinal tract of a patient. A magnet was positioned in the tip of the intubation tube. An electromagnet was provided for generating a magnetic field which coupled the magnet in the intubation tube and developed an attractive or repulsive force on the magnet, whereby the intubation tube could be directed in a predetermined direction. However, this patent was not directed to adjusting or manipulating the intestines, e.g., retraction, suspension or longitudinal translation of intestine segments to assist in the performance of laparoscopic surgery. This patent was merely directed to intestinal intubation, including an electromagnetic means which made it suitable for manual manipulation during an intubation operation.

U.S. Pat. No. 3,474,777, patented Oct. 28, 1969, by F. H. J. Figge et al, titled "Method of Administering Therapeutic Agents", provided a method of localizing a therapeutic agent at a preferred treatment site within an organism by injecting the agent into the organism in association with a magnetically-responsive substance. The agent and the magnetically-responsive substance were concentrated at the preferred treatment site by the application of magnetic fields to the organism. Microcapsules and/or particles adaptable to injection and having a maximum size of about five microns included a therapeutic agent in association with a magnetically-responsive substance. The patent taught that the magnetically-responsive substance may be coated with, or dispersed within, a therapeutic agent or, conversely, that a magnetically-responsive substance may be used to coat or partially to coat a therapeutic agent, or as a matrix for the agent. When the particles were employed in the form of microcapsules, the magnetically-responsive substance could be within the capsule shell, or the magnetic substance could form part of a shell encapsulating a therapeutic agent. However, this patent was not directed to adjusting or manipulating the intestines, e.g., retraction, suspension or longitudinal translation of intestine segments to assist in the performance of laparoscopic surgery. On the other hand, this patent was only concerned with the provision of means for localizing therapeutic agents within the organism at those sites which were specifically desired to be treated with the therapeutic agent, without being dispersed generally throughout the organism.

U.S. Pat. No. 3,794,041, patented Feb. 26, 1974, by E. H. Frei et al, titled "Gastrointestinal Catheter", provided a gastrointestinal catheter of elongated flexible shape, including ferromagnetic material. When the catheter was inserted into the cavity of a body part, it would be attracted by a magnet external of the body in order to manipulate the body part with the catheter. The ferromagnetic material included a plurality of ellipsoidal beads of soft iron in the catheter in closely-adjacent spaced relationship therein over a substantial length thereof. The soft iron ellipsoidal beads were. fixed in the relationship by the resiliency of the flexible tubular members. The patentee further taught the provision of a coating of a plastic, e.g., polyethylene, of adequate thickness, on the iron beads. In use, the gastrointestinal catheter was adapted, when inserted into the cavity of a body part, to be uniformly and unidirectionally attracted by a magnet which was external of the body for desired displacement of the body part substantially without the application of torque to the beads. However, this patent was not directed to adjusting or manipulating the intestines, e.g., retraction, suspension or longitudinal translation of intestine segments to assist in the performance of laparoscopic surgery. On the other hand, this patent was only concerned with a solution to the problem that, in certain types of disease, the only effective treatment consisted of massive irradiation of the affected organ by concentrating the treatment at that organ.

U.S. Pat. No. 4,364,377, patented Dec. 21, 1987, by F. W. Smith, titled "Magnetic Field Hemostasis", taught a method for staunching blood flow from a bleeding gastrointestinal lesion. The method included introducing, into the gastrointestinal tract, a suitable tamponading mass having ferromagnetic properties. One such suitable tamponading mass was a mixture of finely divided iron particles and vegetable oil which may be introduced through an endoscopic catheter. Once in the gastrointestinal tract, the tamponading mass was moved as necessary to cover and press upon the bleeding lesion by a magnetic field which was generated outside the body, e.g., by an electromagnet. The positioning was under the direct visual control of the endoscopist. However, this patent was not directed to adjusting or manipulating the intestines, e.g., retraction, suspension or longitudinal translation of intestine segments to assist in the performance of laparoscopic surgery. On the other hand, this patent was only concerned with the difficulties of stopping the bleeding of gastrointestinal lesions, e.g., acutely bleeding ulcers.

U.S. Pat. No. 4,428,366, patented Jan. 31, 1984, by E. Findl et al, provided an electromagnetic apparatus and method for the reduction of serum glucose levels. The apparatus included a table upon which the patient lay, and a coil, both above and below, the table. The apparatus applied a uniform, monopolar pulsed magnetic field to cause electric currents and field generation in an animal. The pulsed magnetic fields were obtained by transmitting individual pulses of direct current to Helmholtz coils, which were located on opposite sides of the patient. However, this patent was not directed to adjusting or manipulating the intestines, e.g., retraction, suspension or longitudinal translation of intestine segments to assist in the performance of laparoscopic surgery.

U.S. Pat. No. 5,183,456, patented Feb. 2, 1993, by A. R. Liboff et al, provided a method and apparatus for the treatment of cancer. The apparatus included a magnetic field generator for producing a controlled, fluctuating, directionally-oriented magnetic field which was parallel to a predetermined axis projecting through a malignant neoplasm. A field detector measured the magnetic flux density along the predetermined axis. The applied magnetic field included a full-wave rectified signal which oscillated at predetermined frequencies to maintain a preselected ratio of frequency to the effective flux density. This ratio was maintained by adjusting the frequency of the fluctuating magnetic field and/or by adjusting the intensity of the applied magnetic field after nulling out the local magnetic field at that region containing the neoplasm. However, this patent was not directed to adjusting or manipulating the intestines, e.g., retraction, suspension or longitudinal translation of intestine segments to assist in the performance of laparoscopic surgery.

U.S. Pat. No. 5,305,749, patented Apr. 26, 1994, by A. J. Li et al, provided MRI systems and methods utilizing a C-shaped main polarizing magnet with opposing pole faces which were situated in approximately-parallel horizontal planes above and below the image volume. That patent provided a patient transport bed that could be movably telescoped over at least a portion of the lower pole face of a C-shaped MRI polarizing magnet, while simultaneously retaining substantially unaltered adjacent open-accessibility to a patient who was disposed on the bed. Thus, this patent merely provided a system in which magnetic poles were provided both above and below the patient. However, this patent was not directed to adjusting or manipulating the intestines, e.g., retraction, suspension or longitudinal translation of intestine segments to assist in the performance of laparoscopic surgery.

U.S. Pat. No. 5,437,600, patented Aug. 1, 1995, by A. R. Liboff et al, provided a method and apparatus for the treatment of cancer. The method included first determining a desired composite magnetic flux having a static field component for treatment of a cancer. Then a patient was placed inside. A container and associated magnetic field generator. A fluctuating magnetic flux was applied to the patient in the associated magnetic field generator along an axis. The actual composite magnetic flux along the axis in the patient was sensed. The actual composite magnetic flux included a component of the fluctuating applied magnetic flux and a component of the naturally-existing static magnetic flux. The actual composite magnetic flux to the desired composite magnetic flux was compared. An error value was then determined. The applied magnetic flux was then modified to correct the error value. However, this patent was not directed to adjusting or manipulating the intestines, e.g., retraction, suspension or longitudinal translation of intestine segments to assist in the performance of laparoscopic surgery.

U.S. Pat. No. 5,529,568, patented Jun. 25, 1996, by R. Rayman, provided a novel operating table system. The operating table system included a table which was formed of non-magnetic material. A support was provided for such table. Magnetic means were provided for applying a magnetic field around a defined area of the table. The magnetic means included one pole below the table, and a second pole was disposed a selected spaced-distance above the table. The second pole included controls for selectively focusing and translating the electromagnetic field by way of manipulation of the second pole.

U.S. Pat. No. 5,593,379, patented Jan. 14, 1997, by R. Rayman, provided an improvement in a method for carrying out laparoscopic surgery on an intestine of a patient. The improvement included establishing discrete magnetic zones within the intestine, by having the patient ingest a magnetic medium. An electromagnetic field which could be focused and translated around the patient was induced by means of a particularly-described electromagnet. Poles of the magnetic medium which were within the intestine were attracted to a pole of the electromagnet. The intestine was manipulated by suspension, or retraction, or lengthwise translation of the entire intestine which was in a segment-by-segment fashion by the essential step of selectively focusing and translating the electromagnetic field by way of manipulation of the upper magnetic pole. The upper magnetic pole included a plurality of displaceable expandable pole heads which were supported on a rotatable shaft magnet, and the electromagnetic field was focused and translated by means of rotation of the rotatable shaft magnet of one of such expandable pole heads; or the upper electromagnetic pole included expandable heads supported in a rotatable shaft magnet, and the electromagnetic field was focused and translated means of displacement of one of the expandable pole heads transversely with respect to the patient; or the upper electromagnetic pole included a plurality of magnetizable rotatable helical shafts and the electromagnetic field was focused and translated by rotation of one of the magnetizable rotatable helical shafts; or the upper electromagnetic pole included a series of magnetically-active wire coils, the electromagnetic field was induced by passing a controlled DC voltage through the magnetically-active wire coils, and the electromagnetic field was focused and translated by controlling the DC voltage to selected ones of the magnetically-active wire coils.

U.S. Pat. No. 5,667,469, patented Sep. 16, 1997, by X. Zhang et al, provided a strong magnetism therapeutic apparatus with permanent-magnets which were rotatable at low frequency. The rotatable permanent-magnet set included a base set made of magnetic material which was fixed on a plate which was capable of rotating in both directions. At least two adjacent permanent-magnet sets for producing strong magnetic fields were secured to the base set and were separated by an isolating block which was made of non-magnetic material. A pole head was secured to the upper surface of each permanent-magnet set. The penetrating depth within the object to be treated was up to about 500 mm. However, this patent was not directed to adjusting or manipulating the intestines, e.g., retraction, suspension or longitudinal translation of intestine segments to assist in the performance of laparoscopic surgery.

U.S. Pat. No. 5,788,624, patented Aug. 4, 1998, to H. Lu et al, provided a magnetic therapy and a magnetic-field scanning physiotherapeutic device. The physiotherapeutic treatment device included a bed, two magnets straddling on either side of the bed, a mechanical-electrical transmission system, and an electric control system. Therapeutic and health-care effect was said to be achieved by means of magnetic field scanning of the body of the patient. The patient lay on the bed facing upward while the two magnets, at properly adjusted heights and actuated by the control panel, moved horizontally along the body of the patient receiving the treatment. However, this patent was not directed to adjusting or manipulating the intestines, e.g., retraction, suspension or longitudinal translation of intestine segments to assist in the performance of laparoscopic surgery.

U.S. Pat. No. 5,945,702, patented Aug. 31, 1999, by J. C. Chan et al, provided a movable magnet transmitter for inducing an electrical current in an implanted coil. In such system, an external power head was energized by a motor causing movement of an element that produced a varying magnetic field, thereby inducing power in an implanted receiver coil within the body of a patient. The external power head included either one or more moving permanent magnets, or one or more moving elements that varied the magnetic flux coupled to the implanted receiver coil. As a result of the varying magnetic field experienced by the implanted receiver coil, an electric current flowed from the implanted receiver coil to energize an implanted medical device.

SUMMARY OF THE INVENTION

Aims of the Invention

Thus, none of the above prior art, with the exception of Applicant's two above-identified patents, was directed to assisting in laparoscopic surgery techniques. In particular, none of such prior patents was directed to the essence of the present invention, namely the provision of magnetic, e.g., electromagnet, means and method for the manipulation of the intestines, e.g., retraction, suspension or longitudinal translation of intestine segments to assist in the performance of laparoscopic surgery.

Accordingly, the present invention has for its main object the provision of a magnetic retraction system, for adjusting and/or manipulating intestine segments to assist in laparoscopic surgery.

Another object of the present invention is the provision of a method using magnetism for adjusting and/or manipulating intestine segments to assist in laparoscopic surgery.

Statement of Invention

This invention provides an magnetic retraction system for assisting in laparoscopic surgery on a patient. Such magnetic retraction system includes a articulatable arm; means securing one end of articulatable arm to a support means; magnetic means which are disposed at another end of the articulatable arm, for applying a magnetic field around a defined area below that of the articulatable arm, the magnetic means including an upper magnetic pole; a lower magnetic pole comprising an opposite pole which has been induced through polarization of magnetic or magnetizable material within the intestine of the patient, the patient being disposed below the upper magnetic pole; and means which are operatively-associated with the upper pole and which are selectively-engage able to adjust the strength of the magnetic field, and/or to adjust the upper pole in height above the patient, and/or in tilt, and/or in roll.

This invention also provides a method for assisting in the laparoscopic surgery of a patient, to enable adjusting and/or manipulating intestine segments. The method includes introducing a viscous medium including magnetic or magnetizable elements therein into the intestine of the patient to provide a magnetic or magnetizable zone within a segment of said intestine. An upper pole of a magnetic means is supported above the patient. A magnetic field is applied around the patient, by means of the upper magnetic pole which is spaced above the patient. A lower opposite magnetic pole is induced by polarization of magnetic or magnetizable elements carried by the viscous medium within the intestine. Segments of the intestine which constitutes the lower opposite magnetic pole are attracted towards the upper magnetic pole. The strength and orientations of the magnetic field around the patient is varied during the laparoscopic surgery to adjust and/or manipulate the intestine.

Other Features of the Invention

By two features of the magnetic retraction system of this invention, the magnetic means comprises an electromagnet; or the magnetic means comprises at least one permanent magnet.

By two other features of the magnetic retraction system of this invention, and/or the above features thereof, the support means comprises a wall of an operating room; or the support means comprises the ceiling of an operating room; or the support means comprises a base of a cart, e.g., a wheeled cart.

By two specific features of the magnetic retraction system of this invention and/or the above features thereof, the base of the cart supports the magnetic means by way of an upwardly-extending, articulatable arm; or the base of the magnetic means is curved to approximate the curvature of the abdomen of a patient.

By another specific feature of the magnetic retraction system of this invention where the magnetic means comprise an electromagnet and/or the above features thereof, the magnetic retraction system includes means which are operatively-associated with the upper pole and which are selectively-engageable to adjust the strength of the electromagnetic field of the upper pole.

By another specific feature of the magnetic retraction system of this invention, and/or the above features thereof, the opposite magnetic pole which is induced within the intestine of the patient is provided by polarization of a plurality of coated particles of magnetic or magnetizable material which are contained in a viscous medium, e.g., glycerol. By a particular feature of that specific feature, the coated particles comprise a plurality of plastic-coated iron spheres, or cellulose-coated iron spheres, or acrylic-coated iron spheres, or plastic-coated steel spheres, or cellulose-coated steel spheres, acrylic-coated steel-spheres, or plastic-coated nickel alloy spheres, or cellulose-coated nickel alloy spheres, acrylic-coated nickel alloy spheres, or plasticcoated ALNICO™ spheres, or cellulose-coated ALNICO™ spheres, acrylic-coated ALNICO™. By a second particular feature of that specific feature, the plastic of the plastic-coated spheres is a food-grade synthetic plastic material, e.g., polyethylene.

Electromagnetic means are well known in the art. One such conventional electromagnetic means could comprise an upper magnetic pole comprising a magnetic core, a coil surrounding one portion of the core, the coil being adapted to be supplied with current, and a pole head which is disposed a selected, spaced-distance above the magnetic retraction system, and a lower magnetic pole comprising a lower induced magnetic pole which is provided by a plurality of magnetic or magnetizable spheres within the intestine of a patient. The coil could comprise a steel core, which is encased in a synthetic plastic casing. The coil could comprise a plurality of individual coils, which are encased in a synthetic plastic casing, e.g., polytetrafluoroethylene.

By two features of the method of this invention, the step of supporting the upper pole comprises an electromagnetic pole; or the step of supporting the upper pole comprises supporting at least one permanent magnet.

By to features of the method of this invention, where the upper supported pole is an electromagnetic pole, the step of varying the strength of the magnetic field comprises varying the electromagnetic field by controlling the voltage to a single magnetic coil surrounding the upper magnetic pole; or by controlling voltage to selected ones of individual coils constituting the upper magnetic coil.

By another feature of the method of this invention, and/or the above features thereof, the step of varying the orientation of the magnetic field comprises adjusting the upper pole in height above the patient, and/or in tilt, and/or in roll.

By yet another feature of the method of this invention, and/or the above features thereof, the step of adjusting and/or manipulating the intestine comprises: the suspension of an intestine segment; or the retraction of an intestine segment; or lengthwise translation of the entire intestine in a segment-by-segment fashion.

By still another feature of the method of this invention, and/or the above features thereof, the step of introducing a viscous medium, magnetic or magnetizable elements comprises: introducing a viscous medium containing a plurality of coated particles of magnetic or magnetizable material; or introducing a viscous medium containing a plurality of plastic-coated, iron spheres, or introducing a viscous medium containing cellulose-coated iron spheres, acrylic-coated iron spheres, or introducing a viscous medium containing plastic-coated steel spheres or introducing a viscous medium containing cellulose-coated steel spheres, or introducing a viscous medium containing acrylic-coated steel spheres, or introducing a viscous medium containing acrylic-coated nickel-alloy spheres or introducing a viscous medium containing cellulose-coated nickel alloy spheres, or introducing a viscous medium containing acrylic-coated nickel alloy spheres, or introducing a viscous medium containing plastic-coated ALNICO™ spheres, e.g., or introducing a viscous medium containing cellulose-coated ALNICO™ spheres or introducing a viscous medium containing acrylic-coated ALNICO™, wherein the spheres are about 2 to 3±1 mm in diameter; and/or wherein the viscous medium is glycerol; or introducing a viscous medium containing a ferromagnetic fluid which becomes gel-like and magnetic in the presence of a magnetic field; and/or wherein a food-grade synthetic plastic material, e.g., polyethylene.

Generalized Description of the Invention

In more general terms, in the present invention, a magnetic retraction system is provided in order to adjust and/or manipulate the intestines magnetically to assist in laparoscopic surgery, without any physical contact with the intestines. Such magnetic retraction system is capable of having its magnetic field adjusted, to provide specific movement of the complete intestine length to assist in laparoscopic surgery.

The novel magnetic retraction system of an embodiment of this invention could optionally include a magnetically-inert patient table, which may be is adjustable in height, and/or in tilt, and/or in roll. Alternatively and/or in addition, the novel magnetic retraction system of this invention may include laparoscopic instruments which are magnetically-inert.

The magnetic retraction system includes a supported magnet, which could be an electromagnetic core surrounding an upper pole of the electromagnet. The upper pole of the electromagnet, e.g., a North pole, is positionable above the patient. The lower pole, e.g., a South pole, is induced in the intestine of the patient by polarization. The induced pole is provided when a viscous fluid containing magnetic or magnetizable particles is introduced into the patient, to provide magnetic or magnetizable zones within the intestine. The viscous fluid includes magnetic or magnetizable elements, or a ferromagnetic fluid which becomes gel-like in the presence of a magnetic field. When an electromagnetic field is induced above the body of the patient by the upper (North) pole, a lower (South) pole is induced in the intestine of the patient which contains such magnetic or magnetizable material by polarization. Controlled adjustment of the electromagnetic field and/or the position of the upper (North) pole enables adjustment and/or manipulation of the intestines.

The electromagnetic field may be adjusted above the body of the patient by manipulation of the magnetic field by controlling the magnetic coils, and/or by raising or lowering the upper (North) pole, and/or by tilting the upper (North) pole, and/or by rolling the upper (North) pole.

The magnetic retraction system of this invention allows an intestine segment to be attracted by the magnetic field and to be suspended for adjustment and/or manipulation. Then, the magnet field and/or the orientation of the upper (North)

pole is adjusted in concert with the surgical operation to provide controlled adjustment and/or manipulation of the intestine.

The present invention thus provides a magnetic retraction system which will assist and enable the magnetic adjustment and/or manipulation of intestine segments during laparoscopic surgery. Such manipulations include the suspension, or the retraction of an intestine segment, or the lengthwise translation of the entire intestine in a segment-by-segment fashion (i.e., "running" the intestine).

In the practice of this invention, a magnetically-attractive viscous medium (as previously-described) is introduced into the patient pre-operatively, and is preferably distributed evenly in the intestinal tract. The magnetic field is applied over the abdomen intraoperatively, and manipulation of the field thereby translates intestine lengths within the abdomen.

One embodiment of a magnetic medium which may be used in the practice of this invention which provides the induced lower (South) pole of the electromagnet is one which contains magnetically-attractive, magnetizable particles which are carried by a viscous fluid. The viscous fluid serves to minimize coalescence of particles, when under the influence of the electromagnetic field. The ideal shape, size, and distribution density of the particles may be empirically-derived by practice. The magnetic or magnetizable material may be of soft iron spheres which are provided with a protective coating, or of steel spheres which are provided with a protective coating, or of a nickel-alloy spheres which are provided with a protective coating, or of ALNICO™ spheres which are provided with a protective coating. The protective coating may be plastic, namely a food-grade plastic, e.g., polyethylene or cellulose or acrylic. The spheres may be about 2 mm to about 3 mm ±0.01 mm in diameter. A spherical shape and maximal diameter of about 2 mm to 3 mm is believed to be optimal. In respect of ideal particle distribution density and size, such spheres of about 2 mm to 3 mm diameter, which are spaced at one per about 0.5 cm$^2$ to 1 cm$^2$ apart may be used.

Another embodiment of a magnetic medium of this invention which provides the lower (South) pole of the electromagnet is a commercially-available ferromagnetic fluid, which becomes gel-like under the influence of a magnetic field.

The strength of the magnetic field in this invention, which may be produced by an electromagnet, or by one or more strategically-placed permanent magnets, should preferably be between about 0.1 tesla and about 0.5 tesla. Any non-ideal distribution of magnetic particles within the intestine may be compensated by an adjustment of the magnetic force.

BRIEF DESCRIPTION OF THE DRAWINGS

In the accompanying drawings,

FIG. 2 is a side elevational view of one embodiment of a magnetic retraction system of this invention;

FIG. 3 is a side elevational view of a second embodiment of a magnetic retraction system of the invention;

FIG. 4 is a side elevational view of a third embodiment of a magnetic retraction system of this invention in combination with a magnetically-inert operating table;

DESCRIPTION OF PREFERRED EMBODIMENTS

Figure 1:
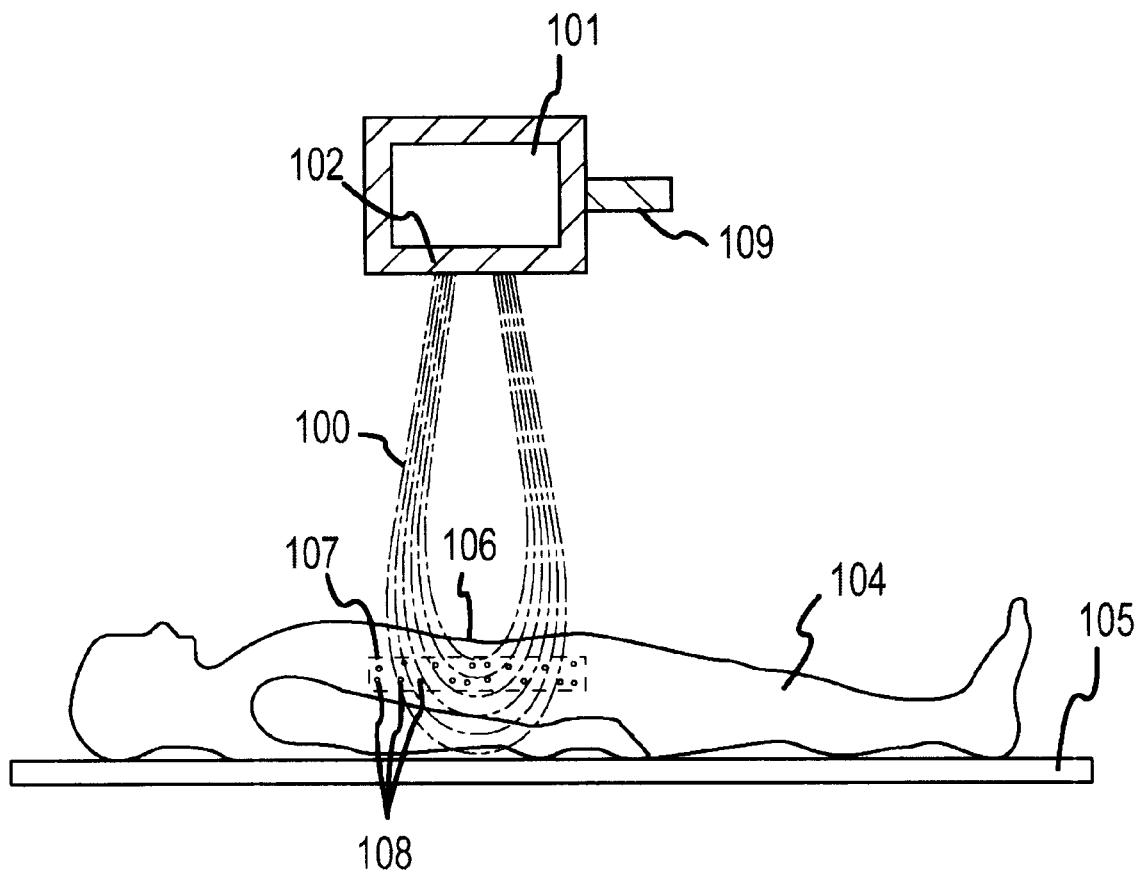
FIG. 1 is a schematic view showing the concept of magnetic manipulation.

Description of FIG. 1

As seen in FIG. 1, a magnetic field 100 is produced by, e.g., an electromagnet 101 which is constituted by an upper (e.g., North) pole 102, which is spaced a selectable distance 103 above a patient 104 resting on an operating table 105. The magnetic field 100 penetrates the abdominal wall 106 of the patient 104, and passes through the intestine segment wall 107. A magnetic or magnetizable medium 108, e.g., plastic-coated iron pellets in a viscous medium, has been introduced pre-operatively into the intestine segment 107, via a nasogastric tube (not shown). The upper (e.g., North) pole 102 provides magnetic field lines 100, which pass through the plastic-coated iron pellets, provide an induced lower (e.g., South) pole 108 by polarization. The simple interaction between the magnetic, upper (e.g., North) pole 102 and the induced magnetic field defining the lower (e.g., South) pole 108, determines the success of intestine attraction in the carrying out of the method of an embodiment of this invention.

It is known that magnetic force decays with distance away from the magnet face in approximately a cubic manner (i.e., F is inversely proportional to $X^3$, where X is distance). An increase in the number of wire turns around the electromagnet core, and the shape of the core itself will increase the magnetic force produced. Liquid cooling of the wire coils may be required to minimize resistance, and therefore allow for a greater current passage and for a greater magnetic force. The electromagnetic upper (e.g., North) pole may be controllably-manipulated in respect of the distance above the patient (in height), and/or the tilt and/or the roll with respect to the patient, which of course provides the induced magnetic lower (e.g., South) pole (107). The upper (e.g., North) pole 102 is provided with a handle 109, whereby the upper (e.g., North) pole 102 may be manually-manipulated in height, and/or in tilt and/or in roll. The handle 109 may also include a control switch (not seen) to control the strength of the magnetic field.

In respect of magnetic field interference, the present steel composition of laparoscopic instruments, e.g., the thin, long-handled instruments, the long gripping instruments, the long camera scope, etc. may interfere with the electromagnetic field. It is, therefore, desirable to use magnetically-inert such laparoscopic instruments. In addition, the operating table 105 should be made of magnetically-inert materials.

Description of FIG. 2

FIG. 2 illustrates one embodiment of a magnetic retraction system 200. This magnetic retraction system 200 consists of an electromagnet 201 which includes a suitable articulatable support 202. This articulatable support 202 is shown in this embodiment as a depending, downwardly-depending articulatable leg 203 to extend downwardly to above the body of a patient (not shown), where the focusable electromagnetic head 204 is disposed. The depending, downwardly-depending articulatable leg 203 is secured to ceiling 205 by means, which are schematically indicated at 206 which enables the depending, downwardly-depending articulatable leg 203, and hence the electromagnetic head 204, to be raised and lowered and/or to tilt and/or to slew so as to provide various orientations of the electromagnetic head in pitch and/or in roll and/or air gap or distance above the patient (not shown). It is noted that the electromagnetic head 204 is provided with a control handle 207.

The connection means 206 to the ceiling 205 to enable the leg 203 to be articulatable, may be any conventional such means, for example, the means for controlling the orientation of an X-ray projector with relation to a patient. Typical examples of such structures are shown in the following U.S. Pat. Nos.: U.S. Pat. No. 2,976,417, patented Mar. 21, 1961, by S. T. Freeman; U.S. Pat. No. 4,426,716, patented Jan. 17, 1984, by M. Muether et al; U.S. Pat. No. 4,475,224, patented Oct. 2, 1984, by V. Grassm; U.S. Pat. No. 4,675,892, patented Jun. 23, 1987, by A. Plessis et al; U.S. Pat. No. 4,829,548, patented May 9, 1989, by J. H. Halm et al; U.S. Pat. No. 4,974,243, patented Nov. 27, 1990, by P. C. McArdle et al; U.S. Pat. No. 5,014,290, patented May 7, 1991, by R. M. Moore et al; U.S. Pat. No. 5,642,392, patented Jun. 24, 1997, by K. Nakano et al; and U.S. Pat. No. 5,666,392, patented Sep. 9, 1997, by J. Ploetz. To the extent that such connection means may be used with the present apparatus, such means are incorporated herein by reference.

A wire coiling 208, e.g., of copper, which may be an individual coil or a plurality of linked coils, produces the magnetic field, and is situated surrounding the depending, downwardly-projecting articulatable leg 203. In one embodiment, the core, e.g., of iron, measures approximately 5 cm×5 cm in cross-section. The wire coiling 208, e.g., of copper, of the electromagnet 201 may require a heat dissipation system (not shown) as well as a power system (not shown) to provide electrical current to produce the electromagnetic field. The electrical current which is provided to the system is adjustable, so that the magnetic field in the air gap or distance between the patient (not seen) and the electromagnetic head 209 causes the induced magnetic field in the intestine of the patient to range from about 0.1 T to about 0.5 T. The field strength required is selected to be that which is necessary to lift and/or manipulate intestinal segments.

Description of FIG. 3

FIG. 3 illustrates a second embodiment of a magnetic retraction system 300. This magnetic retraction system 300 consists of an electromagnet 301 which includes a suitable articulatable support 302. This support 302 is shown, in this embodiment as a depending, downwardly-depending articulatable leg 303 to extend downwardly to above the body of a patient (not seen), where the focusable electromagnetic head 304 is disposed. A horizontal beam 305 is secured to a wall 306 and is connected to the depending, downwardly-depending articulatable leg 303 by means, which are schematically indicated at 307 which enables the depending, downwardly-depending articulatable leg 303, and hence the electromagnetic head 304, to be raised and lowered and/or to tilt and/or to slew so as to provide various orientations of the electromagnetic head in pitch and/or in roll and/or in a air gap or distance above the patient (not shown). It is noted that the electromagnetic head 304 is provided with a control handle 308.

The connection means 307 to enable the leg 203 to be articulatable may be any conventional such means, for example, the means for controlling the orientation of an X-ray projector with relation to a patient. Typical examples of such structures are shown in the following U.S. Pat. Nos.: U.S. Pat. No. 2,976,417, patented Mar. 21, 1961, by S. T. Freeman; U.S. Pat. No. 4,426,716, patented Jan. 17, 1984, by M. Muether et al; U.S. Pat. No. 4,475,224, patented Oct. 2, 1984, by V. Grassm; U.S. Pat. No. 4,675,892, patented Jun. 23, 1987, by A. Plessis et al; U.S. Pat. No. 4,829,548, patented May 9, 1989, by J. H. Halm et al; U.S. Pat. No. 4,974,243, patented Nov. 27, 1990, by P. C. McArdle et al; U.S. Pat. No. 5,014,290, patented May 7, 1991, by R. M. Moore et al; U.S. Pat. No. 5,642,392, patented Jun. 24, 1997, by K. Nakano et al; and U.S. Pat. No. 5,666,392, patented Sep. 9, 1997, by J. Ploetz. To the extent that such connection means may be used with the present apparatus, such means are incorporated herein by reference.

A wire coiling 309, e.g., of copper, which may be an individual coil or a plurality of linked coils, produces the magnetic field, and is situated surrounding the depending, downwardly-depending articulatable leg 303. In one embodiment, the core, e.g., of iron, measures approximately 5 cm×5 cm in cross-section. The wire coiling 309, e.g., of copper, of the electromagnet 301 may require a heat dissipation system (not shown) as well as a power system (not shown) to provide electrical current to produce the electromagnetic field. The electrical current which is provided to the system is adjustable, so that the magnetic field in the air gap or distance between the patient (not seen) and the electromagnetic head 304 causes the induced magnetic field in the intestine of the patient to range from about 0.1 T to about 0.5 T. The field strength required is selected to be that which is necessary to lift and/or manipulate intestinal segments.

Description of FIG. 4

FIG. 4 illustrates a third embodiment of a magnetic retraction system 400. This magnetic retraction system 400 consists of an electromagnet 401 which includes a suitable articulatable support 402. This articulatable support 402 is shown in this embodiment as a depending, downwardly-depending articulatable leg 403 to extend downwardly to above the body of a patient (not seen), where the focusable electromagnetic head 404 is disposed. The patient is adapted to be disposed on a magnetically-inert operating table, indicated generally as 405, which is supported on a conventional base 406 which is adjustable in height and/or in pitch and/or in roll. The downwardly-depending articulatable leg 403 is secured to a ceiling 407 by means which are schematically indicated at 408 which enables the depending, downwardly-depending articulatable leg 403, and hence the electromagnetic head 404, to be raised and lowered and/or to tilt and/or to slew so as to provide various orientations of the electromagnetic head in pitch and/or in roll and/or the air gap or distance 409 above the magnetically-inert operating table 405. It is noted that the electromagnetic head 404 is provided with a control handle 410.

The connection means 408 to enable the leg 403 to be articulatable may be any conventional such means, for example, the means for controlling the orientation of an X-ray projector with relation to a patient. Typical examples of such structures are shown in the following U.S. Pat. Nos.: U.S. Pat. No. 2,976,417, patented Mar. 21, 1961, by S. T. Freeman; U.S. Pat. No. 4,426,716, patented Jan. 17, 1984, by M. Muether et al; U.S. Pat. No. 4,475,224, patented Oct. 2, 1984, by V. Grassm; U.S. Pat. No. 4,675,892, patented. Jun. 23, 1987, by A. Plessis et al; U.S. Pat. No. 4,829,548, patented May 9, 1989, by J. H. Halm et al; U.S. Pat. No. 4,974,243, patented Nov. 27, 1990, by P. C. McArdle et al; U.S. Pat. No. 5,014,290, patented May 7, 1991, by R. M. Moore et al; U.S. Pat. No. 5,642,392, patented Jun. 24, 1997, by K. Nakano et al; and U.S. Pat. No. 5,666,392, patented Sep. 9, 1997, by J. Ploetz. To the extent that such connection means may be used with the present apparatus, such means are incorporated herein by reference.

A wire coiling 411, e.g., of copper, which may be an individual coil or a plurality of linked coils, produces the magnetic field, and is situated surrounding the depending, downwardly-depending articulatable leg 403. In one embodiment, the core, e.g., of iron, measures approximately 5 cm×5 cm in cross-section. The wire coiling 411, e.g., of copper, of the electromagnet 401 may require a heat dissipation system (now shown) as well as a power system (not shown) to provide electrical current to produce the electromagnetic field. The electrical current which is provided to the system is adjustmagnetic reaction system, so that the magnetic field in the air gap or distance 409 between the magnetically-inert operating table 405 and the electromagnetic head 404 causes the induced magnetic field in the intestine of the patient to range from about 0.1 T to about 0.5 T. The field strength required is selected to be that which is necessary to lift and/or manipulate intestinal segments.

Figure 5:
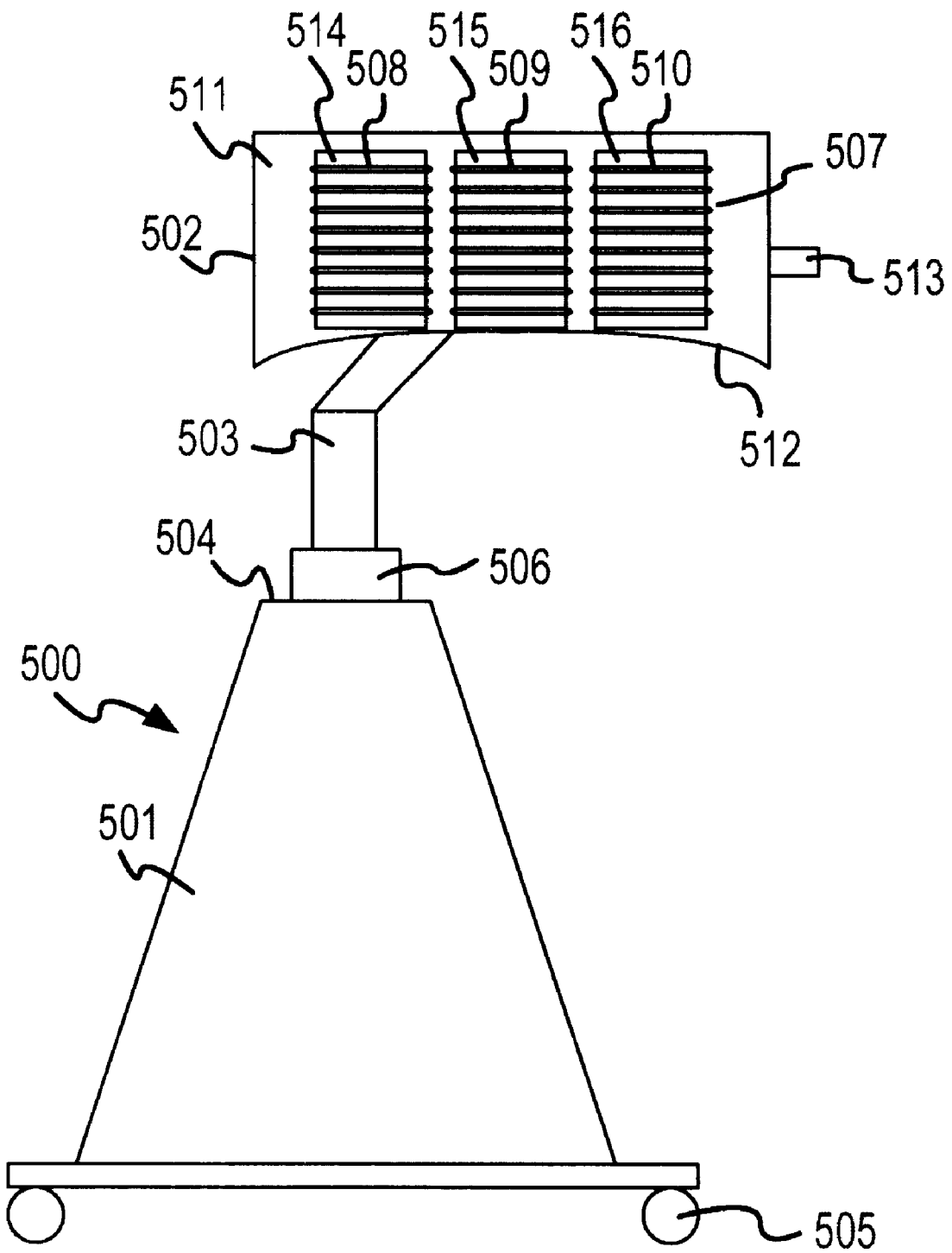
FIG. 5 is a side elevational view of a fourth (and preferred) embodiment of a magnetic retraction system of this invention.

Description of FIG. 5

FIG. 5 illustrates a fourth embodiment of a magnetic retraction system 500. This magnetic retraction system 500 consists of a generally-pyramidal hollow base 501 within which are encased a power unit and suitable controls (not seen) for an electromagnet 502. The base 501 includes suitable wheels 505 by means of which it can be rolled to a magnetically inert operating table (not seen). The electromagnet 502 is supported on an articulatable arm 503 extending upwardly from the top 504 of the base 501 to the bottom of the electromagnet. The arm 503 is connected to the top 504 of the base 501 by means, schematically indicated at 506, which enables arm 503 to be articulatable, which thus enables the electromagnetic head 507 of the electromagnet 502 to be raised and lower and/or to tilt and/or to slew so as to provide various orientations of the electromagnetic head in pitch and/or in roll and/or an air gap or distance above the patient (not seen). The electromagnetic head 507 consists of a plurality, in this case three, coils 508,509,510 which are operated by the power unit. The electromagnetic head 507 is disposed within a case 511 whose lower face 512 is contoured to approximate the curvature of the abdomen of the patient. It is noted that the electromagnetic head 507 is provided with a control handle 513.

Connection means 506 between the top 504 of the base and the arm 503 to enable the arm 503 to be articulatable may be any conventional such means, for example, the means for controlling the orientation of an X-ray projector with relation to a patient. Typical examples of such structures are shown in the following U.S. Pat. Nos.: U.S. Pat. No. 2,976,417, patented Mar. 21, 1961, by S. T. Freeman; U.S. Pat. No. 4,426,716, patented Jan. 17, 1984, by M. Muether et al; U.S. Pat. No. 4,475,224, patented Oct. 2, 1984, by V. Grassm; U.S. Pat. No. 4,675,892, patented Jun. 23, 1987, by A. Plessis et al; U.S. Pat. No. 4,829,548, patented May 9, 1989, by J. H. Halm et al; U.S. Pat. No. 4,974,243, patented Nov. 27, 1990, by P. C. McArdle et al; U.S. Pat. No. 5,014,290, patented May 7, 1991, by R. M. Moore et al; U.S. Pat. No. 5,642,392, patented Jun. 24, 1997, by K. Nakano et al; and U.S. Pat. No. 5,666,392, patented Sep. 9, 1997, by J. Ploetz. To the extent that such connection means may be used with the present apparatus, such means are incorporated herein by reference.

Wire coilings 508,509,510, e.g., of copper, which, as shown in this embodiment, consist of a plurality of linked coils, produce the magnetic field, and are situated surrounding the respective cores 514,515,516 constituting the electromagnetic head 507. In one embodiment, the core, e.g., of iron, measures approximately 5 cm×5 cm in cross-section. The wire coiling 508,509,510, e.g., of copper, of the electromagnet 502 may require a heat dissipation system (now shown) as well as a power system (not shown) to provide electrical current to produce the electromagnetic field. The electrical current which is provided to the system is adjustable, so that the magnetic field in the air gap or distance between the patient (not seen) and the electromagnetic head 507 causes the induced magnetic field in the intestine of the patient to range from about 0.1 T to about 0.5 T. The field strength required is selected to be that which is necessary to lift and/or manipulate intestinal segments.

Figure 6:
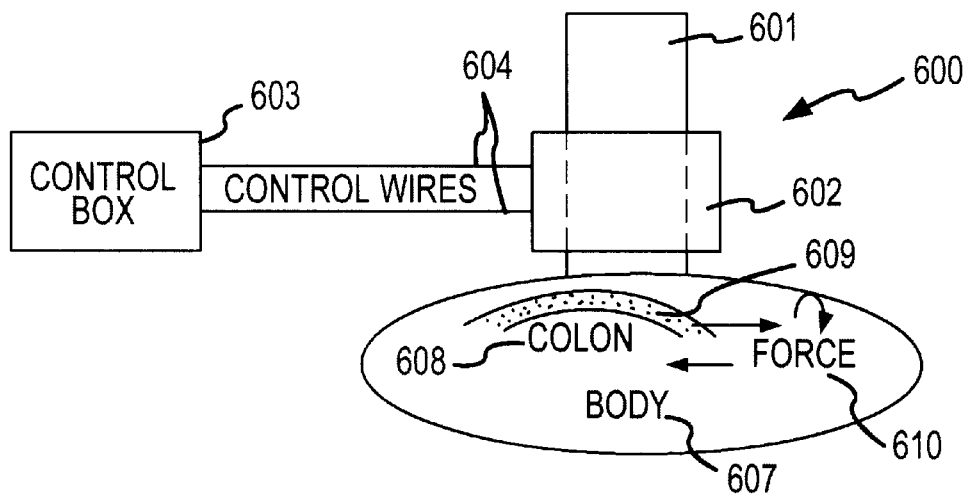
FIG. 6 is a schematic representation and overview of the operating system for the magnetic retraction system of this invention.

Description of FIG. 6

FIG. 6 shows an overview of the general magnetic retraction system 600. The magnetic retraction system includes an upper electromagnet 601, which includes one electromagnetic coil or a plurality of electromagnetic coils 602, and a control box 603 which is connected thereto by control wires 604.

The upper electromagnet 601 is attached to the control box 603 via a low reluctance connection. As noted above, the electromagnetic coil or electromagnetic coils 602 may be single coil or a plurality of series-connected coils. The electromagnetic coil or electromagnetic coils 602 are excited by current waveforms produced by the circuitry associated with the control box 603.

As seen in FIG. 6, the body of the patient 607 includes an intestine (or colon) 608 within which the magnetized particles are sited to provide an induced magnetic lower (or South) pole 609. This provides various forces 610 on the intestine (or colon) 608.

Figure 7:
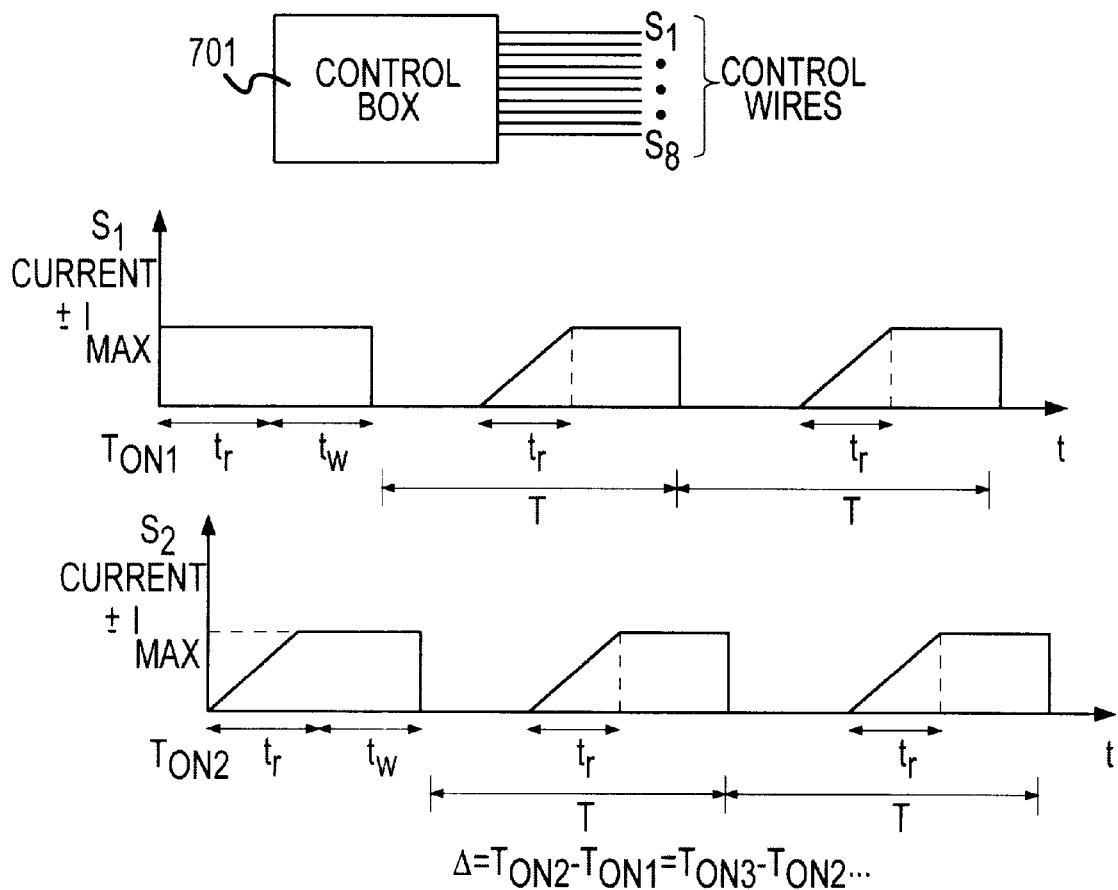
FIG. 7 is a schematic representation of the control box and associated current waveforms.

Description of FIG. 7

The control box 701 outputs the current waveforms shown in FIG. 7 which are outputted by the control wires $S_1$ to $S_8$. The rise time, $t_r$, pulse width, $t_w$, and period, T, can be varied via control knobs (not seen). The phase relationship between the waveforms of each individual coil can also be varied via a control knob (not seen). The polarity of each wave form can be positive or negative, in order to increase the gradient of the produced magnetic field.

Generalized Description of the Operation of the Invention

The use of laparoscopic techniques for performing abdominal surgery is advantageous for the patient (decreased morbidity, etc.), but awkward for the surgeon. This is especially true in intestine surgery, because the small gripping area of laparoscopic instruments make continuous lengths of intestine difficult to manoeuvre. The development of a retraction system, according to the present invention, which is adapted to grip, to retract, or to run intestine lengths extracorporeally, thus would assist and ease the performance of laparoscopic procedures.

The magnetic retraction system of this invention allows an induced magnetic (or South) pole within a segment of the intestine, e.g., by means of a polarization of a viscous ferromagnetic particle-containing solution, or a ferromagnetic fluid which becomes gel-like in the presence of a magnetic field, which has been introduced into the patient and resides within the intestines to be attracted to the upper electromagnet head. This solution is a fluid which should be biologically-inert, and may be a semi-viscous gel (e.g., gelatin or glycerol) containing coated, stainless steel, or other ferromagnetic particles, as previously described, or a ferromagnetic fluid which becomes gel-like in the presence of a magnetic field. The particles may be approximately 1 mm in greatest diameter. The solution is introduced into the patient pre-operatively. Post-operatively, the natural peristaltic movement of the intestines excretes the fluid from the body, without any biologic impact to the patient. Intestinal segment replicas were used in the laboratory to identify the ideal distribution density of ferromagnetic particles. One particle per about 0.5 $cm^2$ to about 1.0 $cm^2$ of surface area of the intestine provided optimal attraction to the upper magnetic (e.g., North) pole.

The magnetic retraction system of this invention produces a specifically-generated and a controlled magnetic field for the manipulation of the intestines. Any other magnetically-active elements within this field can adversely change field characteristics. Therefore, all laparoscopic instruments, e.g., the thin, long-handled surgical instruments, the long camera scope, the long gripping instruments, etc., used for surgical procedures must be magnetically-inert. In addition, the operating table must be magnetically-inert.

Simple attraction of an intestine loop to the inside of the abdominal wall is not sufficient for intestine manipulation. Retraction and translation of intestine segments (i.e., "running" the intestine) is more useful. "Running" of the intestine segments could be done by means of an upper electromagnetic (e.g., North) pole, which can be raised and/or lowered, and/or tilted and/or slewed.

Intestine adhesions generally would not be able to be overcome by the electromagnetic force. In this case, conventional laparoscopic instruments would be used until discrete adhesions are released. Then the method of this invention would be carried out.

Attraction of the induced lower (e.g., South) pole within the intestines towards the upper magnetic (e.g., North) pole is the key to success of the magnetic retraction system of this invention. Force can be increased by using higher current, larger amounts of wire coiling, possibly liquid cooling of wires, and a U-shaped coil design.

The magnetic retraction system described hereinabove, will assist and ease greatly the laparoscopic manipulation of intestine lengths. Therefore, it will both speed the completion of current laparoscopic surgeries and widen the scope of procedures done laparoscopically.

In order to enable magnetic forces to retract, to suspend, or to longitudinally translate intestine segments to ease the performance of laparoscopic surgeries, it was found to be necessary to provide the magnetic field coil above the patient to induce a lower magnetic (e.g., South) pole of the biologically-inert ferromagnetic fluid in the biologically-inert, ferrous particles which have been ingested by the patient preoperatively to be attracted to the upper (e.g., North) pole.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What is claimed is:

1. A magnetic retraction system for assisting in laparoscopic surgery on a patient, said system comprising:
   a) an articulatable arm;
   b) a securing member for securing one end of said articulatable arm to a support member;
   c) a magnet which is disposed at another end of said articulatable arm, for applying a magnetic field around a defined area below said another end of said articulatable arm, said magnet including an upper magnetic pole;
   d) a patient adapted to be disposed below said upper magnetic pole, said patient having ingested a magnetizable or magnetic element whereby, when said patient is disposed prone below said upper magnetic pole, a lower opposite magnetic pole is induced in said patient through polarization of magnetizable material within the intestine of said patient; and
   e) a controllable element which is operatively-associated with said upper pole and which is selectively-controllable to vary the magnetic field, and/or adjust the upper pole in height above said patient, and/or tilt, and/or roll.

2. The magnet retraction system of claim 1, wherein said support comprises a base of a cart.

3. The magnetic retraction system of claim 2, wherein said cart is a wheeled cart.

4. The magnetic retraction system of claim 1, wherein said opposite magnetic pole which is induced within the intestine of said patient is provided by polarization of a plurality of coated particles of magnetic or magnetizable material which are contained in a viscous medium.

5. The magnetic retraction system of claim 4, wherein said viscous medium is glycerol.

6. The magnetic retraction system of claim 4, wherein said coated particles comprise a plurality of plastic-coated iron spheres, or cellulose-coated iron spheres, or acrylic-coated iron spheres, or plastic-coated steel spheres, or cellulose-coated steel spheres, or acrylic-coated steel-spheres, or plastic-coated nickel alloy spheres, or cellulose-coated nickel alloy spheres, or acrylic-coated nickel alloy spheres, or plastic-coated ALNICO™ spheres, or cellulose-coated ALNICO™ spheres, or acrylic-coated ALNICO™ spheres.

7. The magnetic retraction system of claim 6, wherein said plastic of said plastic-coated spheres is a food-grade, synthetic plastic material.

8. The magnetic retraction system of claim 7, wherein said food-grade, synthetic plastic material in polyethylene.

9. The magnetic retraction system of claim 6, wherein said spheres are about 1 mm to about 2 mm±0.1 mm in diameter.

10. The magnetic retraction system of claim 24, wherein said magnet comprises an electromagnet.

11. The magnetic retraction system of claim 1, wherein said magnet comprises at least one permanent magnet.

12. The magnetic retraction system of 1, wherein said support member comprises a wall of an operating room.

13. The magnetic retraction system of claim 1, wherein said support member comprises the ceiling of an operating room.

14. The magnetic retraction system of claim 2, wherein said base of said cart supports said magnet by way of an upwardly-extending said, articulatable arm.

15. The magnetic retraction system of claim 1, wherein a lower face of said upper magnetic pole is curved to approximate the curvature of the abdomen of a patient.

16. The magnetic retraction system of claim 10, including means which are operatively-associated with said upper pole and which are selectively-engageable to adjust the strength of the electromagnetic field of said upper pole.

17. The magnetic retraction system of claim 1, wherein said opposite magnetic pole which is induced within the intestine of said patient is provided by polarization of a ferromagnetic fluid which becomes gel-like and magnetic in the presence of a magnetic field.

18. The magnetic retraction system of claim 1, in combination with a magnetically-inert operating table.

19. The magnetic retraction system of claim 1, in combination with magnetically-inert laparoscopic instruments.

* * * * *